(12) United States Patent
Karvonen et al.

(10) Patent No.: US 9,454,913 B2
(45) Date of Patent: Sep. 27, 2016

(54) SIMULATOR TOOL FOR PHYSICAL EXERCISE DEVICE

(71) Applicant: Polar Electro Oy, Kempele (FI)

(72) Inventors: Sami Karvonen, Travers (CH); Erkki Silvola, Oulunsalo (FI)

(73) Assignee: POLAR ELECTRO OY, Kempele (FI)

( * ) Notice: Subject to any disclaimer, the term of this patent is extended or adjusted under 35 U.S.C. 154(b) by 672 days.

(21) Appl. No.: 13/919,722

(22) Filed: Jun. 17, 2013

(65) Prior Publication Data
US 2014/0372097 A1   Dec. 18, 2014

(51) Int. Cl.
| G06F 13/00 | (2006.01) |
| G06F 19/00 | (2011.01) |
| G09B 19/00 | (2006.01) |
| A61B 5/00 | (2006.01) |
| A61B 5/024 | (2006.01) |

(52) U.S. Cl.
CPC ......... *G09B 19/0038* (2013.01); *A61B 5/0024* (2013.01); *A61B 5/02438* (2013.01); *A61B 5/681* (2013.01); *A61B 5/7278* (2013.01); *G06F 19/3481* (2013.01)

(58) Field of Classification Search
USPC ......... 703/2, 24, 6; 482/1, 8, 9, 57; 345/173
See application file for complete search history.

(56) References Cited

U.S. PATENT DOCUMENTS

| 6,659,916 | B1 * | 12/2003 | Shea | A63B 22/00 482/57 |
| 8,047,965 | B2 * | 11/2011 | Shea | A63B 22/00 482/1 |
| 8,506,370 | B2 * | 8/2013 | Homsi | A63B 24/0021 463/15 |
| 2004/0183787 | A1 * | 9/2004 | Geaghan | G06F 3/0488 345/173 |
| 2005/0075213 | A1 * | 4/2005 | Arick | A63B 24/00 482/1 |
| 2011/0163385 | A1 * | 7/2011 | Chidambarrao | H01L 21/823857 257/369 |
| 2011/0263385 | A1 * | 10/2011 | Shea | A63B 22/00 482/9 |
| 2012/0108394 | A1 * | 5/2012 | Jones | A63B 69/004 482/8 |
| 2013/0217542 | A1 * | 8/2013 | Shea | A63B 22/00 482/8 |

* cited by examiner

*Primary Examiner* — Thai Phan
(74) *Attorney, Agent, or Firm* — Hoffmann & Baron, LLP (57) ABSTRACT

A method, apparatus, and computer program for simulating a sensor device are disclosed. According to an embodiment, the method comprises: executing a simulator program capable of simulating operation of a plurality of exercise sensor devices; selecting a subset of the plurality of exercise sensor devices for simulation, said subset comprising simulated at least one exercise sensor device; establishing a wireless communication link with a counterpart apparatus of a user according to a communication protocol supported by the simulated at least one exercise sensor device; generating measurement data representing measurement data generated by said simulated at least one exercise sensor device; and testing compatibility between the simulated at least one exercise sensor device and the counterpart apparatus by outputting a parameter dependent on the generated measurement data to the display screen for display and to the counterpart apparatus over the communication link in a data structure used by the simulated at least one exercise sensor device.

21 Claims, 4 Drawing Sheets

SIMULATOR TOOL FOR PHYSICAL EXERCISE DEVICE

BACKGROUND

1. Field

The invention relates to the field of physical training devices and to simulating functions of one device in another device.

2. Description of the Related Art

Numerous training measurement devices are available on the markets. These devices include numerous different training computers such as wrist computers, gym devices and, additionally, numerous sensor devices. This creates a great number of different combinations of sensors and counterpart devices and, furthermore, numerous versions of communication and service protocols make it very difficult for a customer to determine whether a specific sensor device is compatible with his/her training computer.

SUMMARY

According to an aspect of the present invention, there is provided a method comprising: executing, in a personal computer apparatus comprising at least one processor, at least one memory including a computer program code, and a display screen, a simulator program capable of simulating operation of a plurality of exercise sensor devices; selecting, by the personal computer apparatus, a subset of the plurality of exercise sensor devices for simulation, said subset comprising simulated at least one exercise sensor device; establishing, in the personal computer apparatus, a wireless communication link with a counterpart apparatus of a user according to a communication protocol supported by the simulated at least one exercise sensor device; generating, in the personal computer apparatus, measurement data representing measurement data generated by said simulated at least one exercise sensor device; testing compatibility between the simulated at least one exercise sensor device and the counterpart apparatus by outputting, by the personal computer apparatus, a parameter dependent on the generated measurement data to the display screen for display and to the counterpart apparatus over the communication link in a data structure used by the simulated at least one exercise sensor device.

According to another aspect of the present invention, there is provided an apparatus comprising: a display screen; at least one processor; and at least one memory including a computer program code. The at least one memory and the computer program code are configured, with the at least one processor, to cause the apparatus to: execute a simulator program capable of simulating operation of a plurality of exercise sensor devices; select a subset of the plurality of exercise sensor devices for simulation, said subset comprising simulated at least one exercise sensor device; establish a wireless communication link with a counterpart apparatus of a user according to a communication protocol supported by the simulated at least one exercise sensor device; generate measurement data representing measurement data generated by said simulated at least one exercise sensor device; test compatibility between the simulated at least one exercise sensor device and the counterpart apparatus by outputting a parameter dependent on the generated measurement data to the display screen for display and to the counterpart apparatus over the communication link in a data structure used by the simulated at least one exercise sensor device.

According to yet another aspect of the present invention, there is provided a computer program product embodied on a non-transitory distribution medium readable by a computer and comprising program instructions which, when loaded into an apparatus, execute a computer process comprising: executing a simulator program capable of simulating operation of a plurality of exercise sensor devices; selecting a subset of the plurality of exercise sensor devices for simulation, said subset comprising simulated at least one exercise sensor device; establishing a wireless communication link with a counterpart apparatus of a user according to a communication protocol supported by the simulated at least one exercise sensor device; generating measurement data representing measurement data generated by said simulated at least one exercise sensor device; testing compatibility between the simulated at least one exercise sensor device and the counterpart apparatus by outputting a parameter dependent on the generated measurement data to the display screen for display and to the counterpart apparatus over the communication link in a data structure used by the simulated at least one exercise sensor device.

Embodiments of the invention are defined in the dependent claims.

BRIEF DESCRIPTION OF THE DRAWINGS

Embodiments of the present invention are described below, by way of example only, with reference to the accompanying drawings, in which.

DETAILED DESCRIPTION

The following embodiments are exemplary. Although the specification may refer to "an", "one", or "some" embodiment(s) in several locations, this does not necessarily mean that each such reference is to the same embodiment(s), or that the feature only applies to a single embodiment. Single features of different embodiments may also be combined to provide other embodiments. Furthermore, words "comprising" and "including" should be understood as not limiting the described embodiments to consist of only those features that have been mentioned and such embodiments may contain also features/structures that have not been specifically mentioned.

Figure 1:
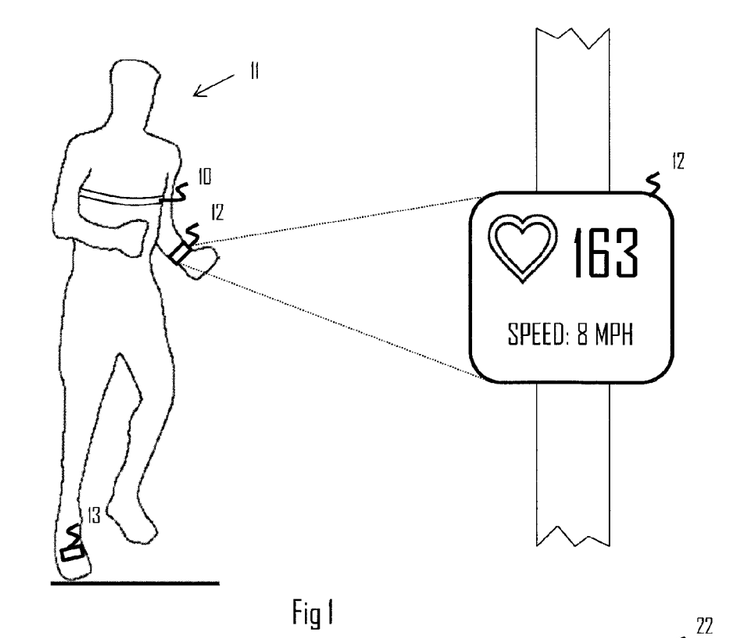
FIG. 1 illustrates a physical training scenario to which embodiments of the invention may be applied.

FIG. 1 illustrates a scenario to which embodiments of the invention may be applied. A user 11 may use various devices in connection with physical training exercises. The user 11 typically carries a training computer 12 such as a wrist computer or another portable training computer which may serve as a personal training instructor and/or a user interface device that provides the user 11 with training instructions and/or displays any data measured during the physical exercise. The training computer 12 may communicate with one or several sensor devices 10, 13 that may be attached to the user's 11 body and configured to measure certain properties during the physical exercise.

A heart activity sensor 10 may be configured to measure user's 11 heart activity during the physical exercise, a motion sensor 13 may measure the user's motion during the exercise, a positioning sensor may measure the user's 11 location during the exercise, a cycling sensor may measure the user's cycling properties during the exercise, a swimming sensor may measure the user's swimming motion, an ambient sensor may measure ambient characteristics such as the climate during the exercise, etc. The motion sensor may comprise one or more accelerometers to measure translational motion, a gyroscope to measure rotational motion, a magnetometer to measure the motion in general, etc. As can be understood, the number of different sensors may be high. In addition, a single manufacturer may provide numerous sensors of various generations designed to measure the same property with each sensor having different functionalities, e.g. different communication protocols. Furthermore, a training computer may be compatible with sensor devices of multiple manufacturers, which broadens the spectrum of sensor devices available to the user 11.

The number of training sensor devices is thus very high. With the constant evolvement of technology, the sensor devices are equipped with new technologies and features, and the user 11 cannot ascertain without considerable effort whether or not the user's 11 training computer 12 is compatible with a certain sensor. This complicates the purchase of new sensors.

Figure 2:
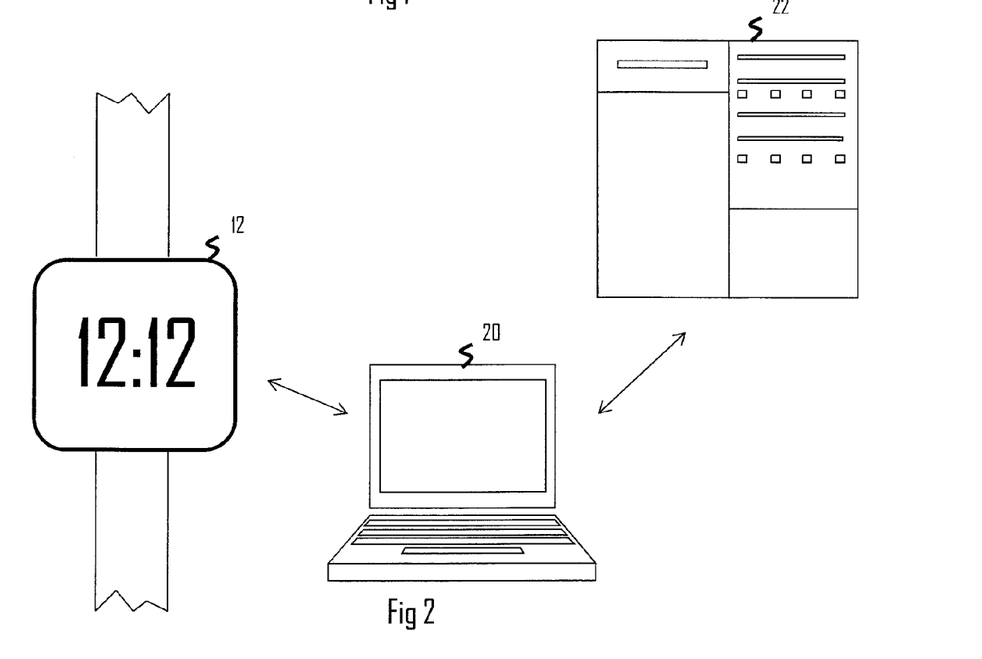
FIG. 2 illustrates a sensor simulation system according to an embodiment of the invention.

FIG. 2 illustrates a system for testing compatibility between the training computer 12 and at least one sensor according to an embodiment of the invention. The system comprises the training computer 12, e.g. the wrist computer. The system further comprises a personal computer 20 which may be a desktop computer or a laptop computer, for example. In an embodiment, the personal computer 20 is a smart phone or, in general, a mobile phone or a tablet computer which provides the user 11 with a better portability to test the compatibility in a sales store, for example. The personal computer 20 may have communication capability with the training computer 12 and, optionally, with a network server 22 in order to download updates etc. The communication between the training computer 12 and the personal computer 20 may be wireless, while the communication between the personal computer 20 and the network server 22 may comprise wired and/or wireless links.

In the above-described embodiments, the training computer 12 is described as a portable apparatus. In other embodiments, the training computer 12 may be any apparatus provided with capability to operate as the training computer. Therefore, the following description uses term counterpart apparatus to refer to that the apparatus functions as a counterpart to the personal computer 20. In an embodiment of the invention, the counterpart apparatus is a gym device, such as a treadmill or bicycle, capable of operating with an exercise sensor.

Figure 3:
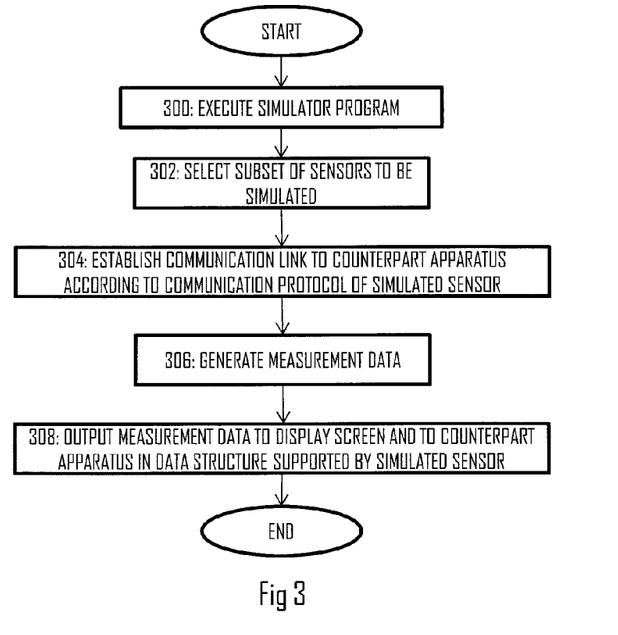
FIG. 3 illustrates a flow diagram of a process for simulating operation of at least one sensor device according to an embodiment of the invention.

According to an embodiment of the invention, the personal computer 20 is configured to simulate the operation of at least one sensor device used in physical training. The personal computer 20 may establish a communication connection with the training computer 12 and operate towards the training computer 12 as the simulated at least one sensor device would operate. Accordingly, the communication link and compatibility between the training computer and the simulated at least one sensor device may be tested. FIG. 3 illustrates a flow diagram of a process the personal computer carries out. Referring to FIG. 3, the personal computer 20 executes a simulator program capable of simulating operation of a plurality of exercise sensor devices. In block 302, the personal computer 20 selects a subset of the plurality of exercise sensor devices for simulation, said subset comprising simulated at least one exercise sensor device. In block 304, the personal computer 20 establishes a wireless communication link with the counterpart apparatus 12 according to a communication protocol supported by the simulated at least one exercise sensor device. In block 306, the personal computer 20 generates measurement data representing measurement data generated by said simulated at least one exercise sensor device. The generated measurement data may be artificially generated in the personal computer 20. In block 308, the compatibility between the simulated at least one exercise sensor device and the counterpart apparatus is tested by outputting, by the personal computer 20, at least one parameter dependent on the generated measurement data to a display screen of the personal computer for display and to the counterpart apparatus 12 over the communication link in a data structure used by the simulated at least one exercise sensor device.

The embodiment described above provides the user 11 with a solution to test the compatibility of his/her training computer with a sensor device before buying the sensor device. It also enables the user 11 to test various features of the sensor device, as further described in greater detail below. As the personal computer 20 simulates also the communication of the sensor device, the counterpart apparatus assumes that it communicates with an actual sensor device, which creates a real-life compatibility testing scenario. The personal computer may further be used as a teaching tool to demonstrate the user how to use the product.

Figure 4:
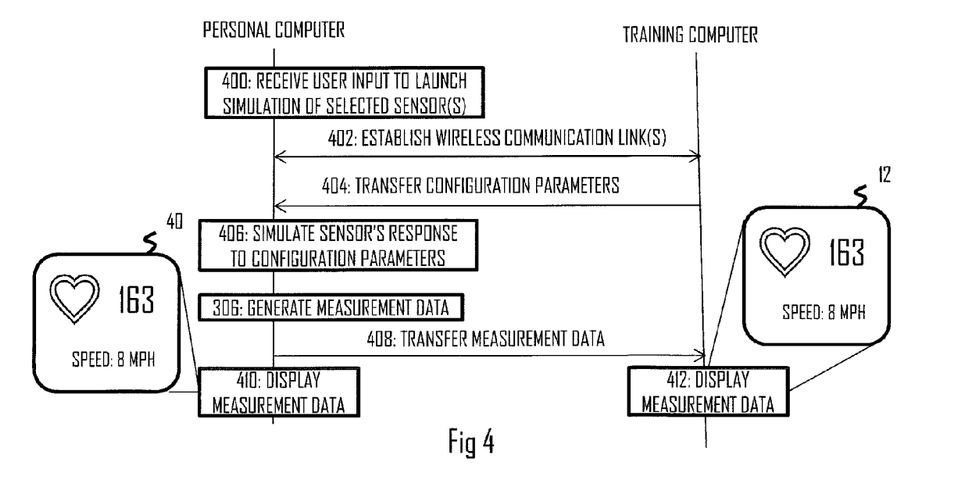
FIGS. 4 to 6 illustrates signalling diagram of sensor simulation procedures according to some embodiments of the invention.

Let us now describe the testing in greater detail with reference to a signalling diagram of FIG. 4. FIG. 4 illustrates the simulation carried out in the personal computer 20 and its communication with the training computer 12 (the counterpart apparatus). Referring to FIG. 4, the personal computer 20 receives user input to launch the simulation of the selected sensor(s). Block 400 may comprise the user operating the personal computer 20, launching a computer program carrying out the simulation and operating a user interface of the computer program. The user interface of the simulator program may comprise selection components enabling the user to select a sensor or a sensor set. The sensors may be classified according to their brand, type, version, etc. The user may select the sensor by inputting an identifier of the sensor to the personal computer. The identifier may be input by inputting a product code in the form of a character string, a quick response (QR) code, a code read through a near-field communications (NFC) tag, or by photograph of the sensor. It may also enable the user to select sensor parameters to be included in the simulation, e.g. input of personal attributes, such as gender, weight, height, age, and/or fitness parameter. The user interface may enable the user to select his/her training computer from a list of training computers and, upon receiving the selection, the personal computer 20 may provide a list of sensor devices compatible with the selected training computer 12. The personal computer 20 may provide a link to a web page that proposes a new/compatible sensor and/or direct the user to a web page where the sensor can be purchased. If the personal computer 20 does not comprise computer program instructions for simulating a sensor device the user 11 has selected, it may be configured to access the network server 22 and retrieve the needed program instructions such that the simulation may be carried out. For example, if the selected sensor device uses a communication protocol not supported by the current version of a transceiver of the personal computer 20, the personal computer 20 may download the configurations of the communication protocol of the selected sensor device form the network server 22.

Upon selecting the sensor(s) to be simulated, the user may trigger the start of the simulation in the personal computer 20. Accordingly, the personal computer launches a computer program that simulates the operation of the selected sensor (s). At this point, the personal computer 20 may provide the user with instructions on the display of the personal computer as how to carry out the testing. For example, the personal computer 20 may instruct the user to operate the training computer to start pairing of the training computer with sensors. The personal computer 20 may configure its wireless transceiver to prepare for establishment of a wireless communication link to the training computer. The wireless transceiver may be configured to support one or more wireless communication protocols, e.g. Bluetooth®, Bluetooth Low Energy, W.I.N.D, Ant by Dynastream, IEEE 802.15, near-field communications (NFC) based on radio frequency identification (RFID) technology, or induction-based transceiver.

In step 402, one or more wireless links are established between the personal computer and the training computer. The number of established links may depend on the number of sensor devices simulated by the personal computer, e.g. the number of established links may be equal to the number of simulated sensor devices. In step 402, the personal computer may configure its wireless transceiver to operate as a wireless transceiver of the simulated sensor device. In the training computer, step 402 may correspond to state-of-the-art establishment of a wireless link with a sensor device although the actual link is established between the training computer 12 and the personal computer 20 and not a real sensor device. The training computer 12 may control the establishment of the wireless communication link, e.g. it may assume a master role.

In step 404, the training computer 12 may transfer configuration parameters to the personal computer 20. The transferred configuration parameters may comprise the user attributes such as age, gender, weight, height, fitness level, and personal training guidance parameters. Further embodiments of the configuration parameters are described below. In an embodiment where the wireless communication link is a Bluetooth communication link, the personal computer 20 may assume a slave mode while the training computer 12 assumes a master mode for the wireless communication link.

In block 406, the personal computer may simulate the sensor's response to the configuration parameters. The personal computer 20 may apply the configuration parameters as inputs to signal processing algorithms used in the simulation of the performance of the sensor device. For example, the personal attributes may be input to an algorithm computing energy consumption in the simulated sensor device. In block 306, the personal computer generates the measurement data and processes the measurement data by using the received configuration parameters. In step 408, the personal computer 20 transfers the processed measurement data to the training computer in a data structure supported by the simulated sensor device and over the established wireless communication link. The transferred measurement data may have been processed in the personal computer 20 according to the configuration parameters transferred in step 404. In step 410, the personal computer 20 displays the measurement data in its display screen 40, while the training computer 12 may display the measurement data in its respective display screen. This dual display of the same measurement data enables the user to verify the compatibility: if the same information is displayed on both displays, the compatibility may be verified; and if no information is displayed on the display of the training computer or different information is displayed on the display screens, there may be a compatibility issue. Since the training computer 12 may compute and display various information derived from the transferred measurement data, the personal computer 20 may be configured to display different types of information derivable from the measurement data known to be displayed by the training computer 12. In an embodiment, the personal computer identifies the model of the training computer in step 402 and determines the types of information the training computer is configured to display in its display screen. The personal computer may then select a corresponding subset of information for display on its own display screen 40. For example, if the transferred measurement data comprises raw heart activity data, e.g. heart rate, the personal computer 20 may compute and display various information derivable from the heart rate, e.g. energy consumption, training load, average heart rate, maximum heart rate, duration of heart rate within each specified training zone (training zone limits may be received as the configuration parameters), etc. The personal computer may compute any one of the above-describe parameters derivable from or dependent on the generated measurement data and output the computed one or more parameters to the to the display screen and to the training computer 12 via the wireless communication link.

The testing of the compatibility may comprise testing whether or not the wireless communication link may be established between the training computer and the simulated sensor device and testing whether or not data may be transferred over the established wireless communication link. For example, Bluetooth specification defines a protocol for establishing and operating the wireless communication links and separate protocols or services defining formats of transferring different types of data over the links. The Bluetooth specification comprises a generic attribute (GATT) profile that defines several services and profiles used in the context of physical exercises, e.g. heart rate profile, heart rate service, personal data service, and runners speed and cadence service. Each of these profiles specifies roles of the communicating parties, in this case the sensor device and the training computer. One of the devices may be a server and the other a client. When establishing the wireless communication link, the training computer may at least initially assume the role of the server and the personal computer simulating the sensor device assumes the client role. At some point of the communication, e.g. when transferring the configuration data in step 404, the roles may be switched such that the personal computer becomes the server and the training computer the slave. Each profile or service further define formats for different types of data transferred between the client and the server, and evolvement of the specification may bring new formats or new types of data that may cause incompatibility between the devices. The format may specify a format of values, e.g. floating point, integer, sizes of the fields in the messages, ranges of the values, precision of the values, etc. The personal data service may define such formats for the following information that may be transferred over the wireless communication link, e.g. in step 404: name, date of birth, weight, height, gender, unique user identifier, activity level in metabolic equivalent of tasks (METs), an energy consumption target for the next exercise, basal metabolic rate (BMR) calories per day, habitual calories per day, exercise calories per day, expended energy target for the day's exercise, aerobic and anaerobic thresholds, maximum heart rate, resting heart rate, maximum oxygen intake VO2max, maximum recommended heart rate, target heart rate zone limits for fat burning and/or aerobic training and/or unaerobic training, waist and hip measurements, and cumulative calories burnt. The aerobic and unaerobic thresholds may be provided separately for different sports types. Each of these values may have a specific data structure in which the information element is communicated. Other services or profiles may define their specific information elements and their respective data structures.

In an embodiment, the data structure in which the personal computer 20 transfers the measurement data over the wireless communication link defines a format dedicated to an information element carrying said generated measurement data in a message transmitted from the simulated at least one exercise sensor device to the counterpart apparatus. Accordingly, the personal computer 20 may select a data transfer service protocol supported by the simulated at least one sensor device amongst a plurality of data transfer service protocols supported by the personal computer apparatus. The personal computer providing capability to simulate various sensor device may also support a plurality of different data transfer service protocols used to transfer the same information, e.g. the same heart rate or another above-described parameter, and select one of them on the basis of the sensor device currently simulated. Then, the personal computer may determine the format of the generated measurement data in the message according to the selected data transfer service protocol and insert the generated measurement data in the determined format into the determined location in the message output to the counterpart apparatus.

Figure 5:
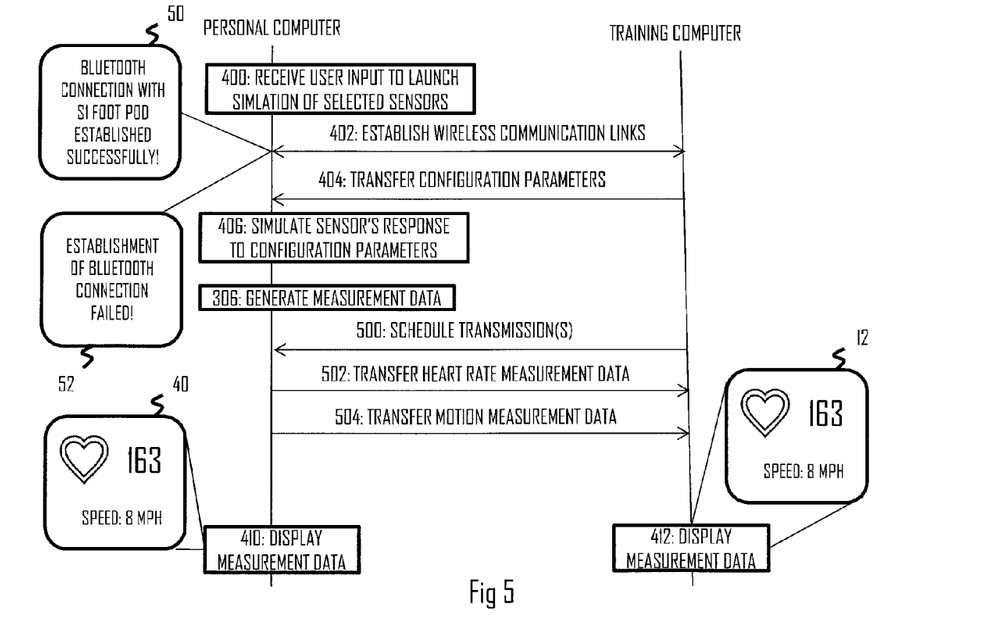

FIG. 5 illustrates a signalling diagram and operation when the personal computer 20 simulates concurrent operation of multiple sensor devices. In FIG. 5, the same reference numbers as used in FIG. 4 represent the same or substantially similar operations. In block 400, the plurality of sensors to be simulated is selected by operating the personal computer 20. In step 402, the personal computer 20 establishes a wireless link with the training computer according for each selected simulated sensor device. The personal computer 20 may determine for each wireless communication link whether or not the establishment of the link was successful and output a display notification of the successful or failed establishment of the link. For example, if a link for a given simulated sensor device was established successfully, the personal computer 20 may display a screen 50 showing that the link with that sensor and the training computer 12 has been established successfully. On the other hand, if a link establishment for a given simulated sensor device resulted in a failure, the personal computer 20 may display a screen 52 showing that the link with that sensor and the training computer 12 has not been established successfully. Steps 404, 406, and 306 may be carried out in the above-described manner. In step 306, the personal computer may generate unique measurement data for each of the simulated sensors. Even if the simulated sensors comprise two sensors that generate similar measurement data, e.g. two pedometers, the personal computer 20 may generate different measurement data for each of them.

In a multi-sensor system with multiple wireless communication links, the training computer 12 may be configured to provide a centralized control for transmissions of the wireless links. The training computer 12 may transmit over each link or as broadcast transmissions scheduling information indicating transmission timing or, in general, transmission resources for each sensor (step 500). In steps 502 and 504, the personal computer transmits measurement data generated for each sensor in a transmission resource scheduled by the training computer for the respective sensors. The measurement data generated for each sensor is naturally transferred over the link established for the respective sensor and with a corresponding data structure. In steps 410 and 412, the measurement data for each sensor is displayed both on the display screen 40 of the personal computer 20 and the display screen of the training computer 12. If the displayed measurement data is the same on both displays, the compatibility is then verified. Otherwise, there may be a compatibility issue.

Providing the multiple displays during the testing may provide indications to the background of a possible compatibility issue. If the establishment of the communication link fails, the communication protocols of the sensor and the training computer may be incompatible. If the establishment of the communication protocol is successful but the displays in steps 410 and 412 show different values for the same measurement parameter, the communication protocol may be compatible but the incompatibility issue may be in the data structures employed by the sensor and the training computer, i.e. the training computer may be able to extract a payload from a frame transmitted by the sensor but not be able to decode the data contained in the payload.

The embodiment of FIG. 5 provides for testing various combinations of sensors and the compatibility in the multi-sensor environment. For example, several different types of sensor may be installed to a bicycle and, concurrently, some sensors may be attached to the user. By using the embodiment of FIG. 5, the user may ensure that further sensors may be added to his/her system without degrading the performance of the system.

The embodiments described above may be used to transfer the measurement data to the training computer in real time or substantially real time. Some compression may be applied to average the measurement data and reduce the amount of transferred traffic but the user may experience the transfer of the measurement data as occurring in real time. The measurement data that may be transferred in this manner may comprise the heart rate data, activity data, motion data, cycling cadence data, cycling power data, instantaneous speed, location data, air pressure, wind speed, temperature, moisture, etc.

Figure 6:
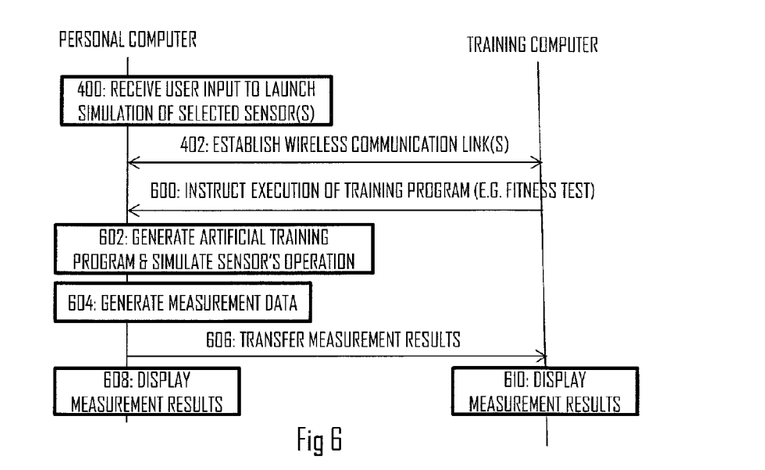

FIG. 6 illustrates an embodiment where the training computer is configured to simulate execution of a training program and transfer measurement results of the training program only after the training program has been simulated. Steps 400 and 402 may equal to those described above. In step 600, the user may operate the training computer 12 or the personal computer and instruct execution of a selected training program. For example, the user may generate a training exercise or a fitness test and instruct the execution of the training program. The training computer may then send instructions about the execution of the training program to the personal computer over the established link(s). The training computer may determine the sensor(s) that are involved in the training program and send the instructions over the links of those sensor(s). For example, when the training program is the fitness test, the user attributes affecting the fitness test and a command to execute the fitness test may be sent over the wireless link of a simulated heart rate sensor. When the training program is a physical exercise, the training computer or the user interface of the personal computer may be operated to generate a real or artificial training program. The training program may be defined by a time series of limits or ranges applicable to the simulated sensors, e.g. heart rate limits or speed limits. The user may also select the sensors that are used in the training program. In block 602, the personal computer generates the artificial training program and launches one or more computer program modules configuring the personal computer to simulate the sensors' operation in the generated training programs. The personal computer may further as inputs any configuration parameters related to the training program. In block 604, the personal computer generates the measurement data related to the training program for each sensor used in the training program. The personal computer may further compute measurement results from the generated measurement data. For example, if the training program was the fitness test, the personal computer may compute a fitness index. If the training program was a physical exercise, the personal computer may compute performance statistics derived from the generated measurement data, e.g. energy consumption, average heart rate, maximum heart rate, average speed, a speed profile during the exercise, etc. If the training program was a jump test employing a motion sensor attachable to the user's foot, the personal computer may compute a jump length/height from the measurement data. In step 606, the personal computer 20 may transmit the measurement results of the training program to the training computer, and in steps 608 and 610 the measurement results are displayed on the display screens of the personal computer and the training computer in order to verify the compatibility.

In an embodiment, the personal computer is used as a maintenance tool to analyse the operation and status of the training computer. For example, the personal computer may be used to connect to the training computer wirelessly in the above-described manner and to extract device information of the training computer, e.g. model or serial number of the training computer. The personal computer may extract error codes of the training computer in a case where the training computer malfunctions, and the personal computer may be used as a diagnostics tool to determine why the training computer malfunctions. Any such information may be stored, and the personal computer may be configured to prepare a diagnostics report showing such information. The personal computer may further be used as a sales tool to demonstrate the operation of the sensors devices together with a real training computer. The embodiment of FIG. 6 may be used to carry out artificial training programs for illustrative purposes without the need for the user or the salesperson to carry out the real physical exercise.

Figure 7:
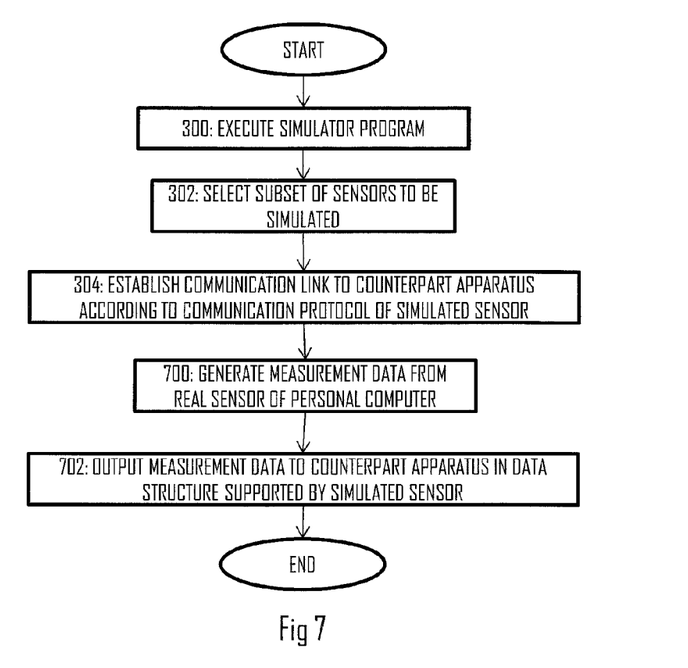
FIG. 7 illustrates a flow diagram of a process for using at least one real sensor in the sensor simulation process according to an embodiment of the invention.

In a further embodiment, the personal computer may be configured to combine the simulation with generation of real measurement data generated by a sensor comprised in the personal computer or connected to the personal computer. Let us consider a situation where the user carries out or is about to carry out a bicycling exercise and the user wants to incorporate positioning data to the training program executed in the training computer. However, the user has no positioning sensor device that is compatible with the training computer. The personal computer, e.g. a mobile phone, equipped with the needed sensor may be configured to execute the above-described simulator program but, instead of generating artificial measurement data, may use a real sensor to generate real measurement data and transfer the real measurement data to the training computer over the established wireless communication link. FIG. 7 illustrates a flow diagram of such a process in the personal computer. Blocks 300, 302, and 304 may correspond to the above-described operations. A logical difference may be that the user may operate the personal computer to operate in the mode where real measurement data of the selected sensor is used. Accordingly, the personal computer may configure the selected real sensor to start measurements and, additionally, the personal computer may launch a simulator program simulating the operation of the corresponding sensor that is compatible with the training computer. In block 700, the real measurement data is generated by the real sensor of the personal computer. The measurement data may be any measurement data used in physical training. The generated real measurement data is then input to the simulator program as the measurement data, and the simulator program simulating the operation of the sensor compatible with the training computer may output the measurement data to the training computer in a data structure supported by the simulated sensor (block 702). Accordingly, the training computer may be provided with the needed measurement data without the user having the actual sensor device compatible with the training computer at hand.

Figure 8:
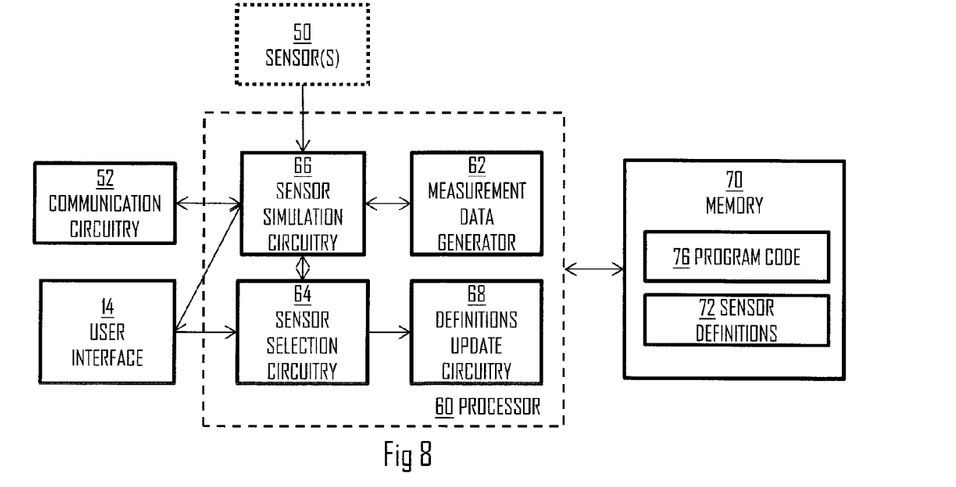
FIG. 8 is a block diagram illustrating the structure of an apparatus according to an embodiment of the invention.

FIG. 8 illustrates a block diagram of a structure of an apparatus according to an embodiment of the invention. The apparatus may comprise at least one processor 60 and at least one memory 70 including a computer program code 76, wherein the at least one memory 70 and the computer program code 76 are configured, with the at least one processor 60, to cause the apparatus to carry out the simulation of at least one sensor device according to any one of the above-described embodiments. The apparatus may comprise or be comprised in the above-described personal computer 20. Embodiments of the apparatus comprise a mobile phone, a tablet computer, a laptop computer, a desktop computer, etc.

Referring to FIG. 8, the processor 60 may comprise a sensor simulation circuitry 66 configured to execute a sensor simulation program simulating the operation of one or more sensor devices. The sensor simulation circuitry may perform the simulation in such manner that the training computer 12 communicating with the apparatus assumes that it communicates with a real sensor device. Inner operation of the sensor simulation circuitry may or may not match with the inner operation of the real sensor device. In other words, the sensor simulation circuitry may emulate the inner operation of the sensor device, if the apparatus comprises similar circuitries as the real sensor device, or the sensor simulation circuitry 66 may merely simulate the operation of dedicated hardware circuits of the sensor device in a computer program executed on a general purpose processor 60. The operation of the sensor simulation circuitry 66 may be triggered by the processor 60 executing a sensor simulation software application and receiving through a user interface 14 a user command to start the simulation. The processor 60 may comprise a sensor selection circuitry 64 configured to determine the simulated sensor device(s) on the basis of user inputs received through the user interface 14. The sensor selection circuitry 64 may then instruct the sensor simulation circuitry 66 to retrieve corresponding sensor definitions from a sensor definitions database 72 stored in the memory 70 and to start execution of the simulation of the selected sensor(s). Upon launching the execution of a sensor device, the sensor simulation circuitry 66 may control a communication circuitry 52 to start establishment of a wireless communication link. In an embodiment, the sensor simulation circuitry 66 may configure the communication circuitry to start a scanning mode in which the communication circuitry scans for training computers attempting to establish wireless pairing. Upon establishing the wireless communication link, the sensor simulation circuitry 66 may output a notification to the user interface 14 to display information on the successful creation of the wireless communication link. Then, the sensor simulation circuitry 66 may cause generation of measurement data associated with the simulated sensor device. In the embodiments using artificial data, the sensor simulation circuitry 66 may activate a measurement data generator 62 comprised in the processor 60. In the embodiments using real measurement data, the sensor simulation circuitry 66 may activate one or more real sensors 50 comprised in or connected to the apparatus. Upon acquiring the measurement data, the sensor simulation circuitry 66 may process the measurement data according to the definitions of the simulated sensor device and/or according to instructions received through the user interface 14 and output the processed measurement data to the user interface 14 of the apparatus and to the communication circuitry 52 to be transmitted to the training computer.

The processor 60 may further comprise a definitions update circuitry 68 configured to connect to the network server 22 and to update the sensor definitions database 72 with new sensor definitions. The operation of the definitions update circuitry 68 may be triggered expiration of a timer counting a time period specifying a periodicity of the update procedure, reception of an input from the sensor selection circuitry 64 indicating the sensor(s) the user has selected for simulation, execution of the sensor simulation software application, etc. The latter embodiments ensure that the latest sensor definitions are always used in the simulation. Additionally, new sensor devices may be proposed to the user for simulation when their definitions are entered into the network server 22.

As used in this application, the term 'circuitry' refers to all of the following: (a) hardware-only circuit implementations such as implementations in only analog and/or digital circuitry; (b) combinations of circuits and software and/or firmware, such as (as applicable): (i) a combination of processor(s) or processor cores; or (ii) portions of processor(s)/software including digital signal processor(s), software, and at least one memory that work together to cause an apparatus to perform specific functions; and (c) circuits, such as a microprocessor(s) or a portion of a microprocessor(s), that require software or firmware for operation, even if the software or firmware is not physically present.

This definition of 'circuitry' applies to all uses of this term in this application. As a further example, as used in this application, the term "circuitry" would also cover an implementation of merely a processor (or multiple processors) or portion of a processor, e.g. one core of a multi-core processor, and its (or their) accompanying software and/or firmware. The term "circuitry" would also cover, for example and if applicable to the particular element, a baseband integrated circuit, an application-specific integrated circuit (ASIC), and/or a field-programmable grid array (FPGA) circuit for the apparatus according to an embodiment of the invention.

The processes or methods described in FIGS. 3 to 7 may also be carried out in the form of a computer process defined by a computer program. The computer program may be in source code form, object code form, or in some intermediate form, and it may be stored in some sort of carrier, which may be any entity or device capable of carrying the program. Such carriers include transitory and/or non-transitory computer media, e.g. a record medium, computer memory, read-only memory, electrical carrier signal, telecommunications signal, and software distribution package. Depending on the processing power needed, the computer program may be executed in a single electronic digital processing unit or it may be distributed amongst a number of processing units.

The present invention is applicable to sensor systems employed in physical training. The communication protocols used, the specifications of sensor systems and the sensor devices, may develop rapidly. Such development may require extra changes to the described embodiments. Therefore, all words and expressions should be interpreted broadly and they are intended to illustrate, not to restrict, the embodiment. It will be obvious to a person skilled in the art that, as technology advances, the inventive concept can be implemented in various ways. The invention and its embodiments are not limited to the examples described above but may vary within the scope of the claims.

What is claimed is:

1. A method comprising:
    executing, in a personal computer apparatus comprising at least one processor, at least one memory including a computer program code, and a display screen, a simulator program capable of simulating operation of a plurality of exercise sensor devices;
    selecting, by the personal computer apparatus, a subset of the plurality of exercise sensor devices for simulation, said subset comprising simulated at least one exercise sensor device;
    establishing, in the personal computer apparatus, a wireless communication link with a counterpart apparatus of a user according to a communication protocol supported by the simulated at least one exercise sensor device;
    generating, in the personal computer apparatus, measurement data representing measurement data generated by said simulated at least one exercise sensor device; and
    testing compatibility between the simulated at least one exercise sensor device and the counterpart apparatus by outputting, by the personal computer apparatus, a parameter dependent on the generated measurement data to the display screen for display and to the counterpart apparatus over the communication link in a data structure used by the simulated at least one exercise sensor device.

2. The method of claim 1, wherein the data structure defines a format dedicated to an information element carrying said generated measurement data in a message transmitted from the simulated at least one exercise sensor device to the counterpart apparatus, the method further comprising in the personal computer apparatus:
    selecting a data transfer service protocol supported by the simulated at least one sensor device amongst a plurality of data transfer service protocols supported by the personal computer apparatus;
    determining the format and a location of the generated measurement data in the message according to the selected data transfer service protocol; and
    inserting the generated measurement data in the determined format into the determined location in the message output to the counterpart apparatus.

3. The method of claim 1, further comprising in the personal computer apparatus:
    receiving configuration parameters from the counterpart apparatus over the established communication link; and
    simulating response of the simulated at least one exercise sensor device to the received configuration parameters.

4. The method of claim 1, further comprising in the personal computer apparatus:
    simulating operation of a plurality of different exercise sensor devices simultaneously;

establishing a plurality of wireless communication links between the personal computer apparatus and the counterpart apparatus, wherein each communication link is associated with a different exercise sensor device;

generating exercise-sensor-specific data for each of the plurality of exercise sensor devices; and testing compatibility in a multi-sensor environment by outputting, by the personal computer apparatus, the generated measurement data to the display screen for display and to the counterpart apparatus over the communication links in data structures supported by the each of the plurality of exercise sensor devices and selected amongst a plurality of data structures supported by the personal computer apparatus for the transfer of the generated measurement data.

5. The method of claim 4, further comprising in the personal computer apparatus:

receiving from the counterpart apparatus scheduling control parameters configuring transmission timing for the plurality of exercise sensor devices; and causing transmission of the generated measurement data of each exercise sensor device in the transmission timing scheduled to said each exercise sensor device.

6. The method of claim 1, further comprising in the personal computer apparatus before said simulation:

receiving, through a user interface, a selection input from the user selecting at least one exercise sensor device to be simulated; and in response to the selection input, selecting a simulator program corresponding to the selected at least one exercise sensor device.

7. The method of claim 1, further comprising in the personal computer apparatus:

when establishing said wireless communication link, determining whether or not the communication link has been established successfully;

upon detecting failed establishment of the communication link, determining whether or not the failure was because of incompatibility between the exercise sensor device and the counterpart apparatus; and upon determining that the failure was because of incompatibility, indicating the incompatibility to the user via the display screen.

8. The method of claim 1, wherein the generated measurement data comprises artificially generated measurement data.

9. The method of claim 1, wherein the generated measurement data comprises real measurement data acquired through at least one sensor of the personal computer apparatus.

10. The method of claim 1, further comprising in the personal computer apparatus: downloading, from a network server computer, program instructions defining simulation parameters for at least one exercise sensor device.

11. An apparatus comprising:
a display screen;
at least one processor; and
at least one memory including a computer program code, wherein the at least one memory and the computer program code are configured, with the at least one processor, to cause the apparatus to:
execute a simulator program capable of simulating operation of a plurality of exercise sensor devices;
select a subset of the plurality of exercise sensor devices for simulation, said subset comprising simulated at least one exercise sensor device;

establish a wireless communication link with a counterpart apparatus of a user according to a communication protocol supported by the simulated at least one exercise sensor device;

generate measurement data representing measurement data generated by said simulated at least one exercise sensor device; and test compatibility between the simulated at least one exercise sensor device and the counterpart apparatus by outputting a parameter dependent on the generated measurement data to the display screen for display and to the counterpart apparatus over the communication link in a data structure used by the simulated at least one exercise sensor device.

12. The apparatus of claim 11, wherein the data structure defines a format dedicated to an information element carrying said generated measurement data in a message transmitted from the simulated at least one exercise sensor device to the counterpart apparatus, and wherein the at least one memory and the computer program code are configured, with the at least one processor, to cause the apparatus to:

select a data transfer service protocol supported by the simulated at least one sensor device amongst a plurality of data transfer service protocols supported by the apparatus;

determine the format and a location of the generated measurement data in the message according to the selected data transfer service protocol; and insert the generated measurement data in the determined format into the determined location in the message output to the counterpart apparatus.

13. The apparatus of claim 11, wherein the at least one memory and the computer program code are configured, with the at least one processor, to cause the apparatus to:

receive configuration parameters from the counterpart apparatus over the established communication link; and simulate response of the simulated at least one exercise sensor device to the received configuration parameters.

14. The apparatus of claims 11, wherein the at least one memory and the computer program code are configured, with the at least one processor, to cause the apparatus to:

simulate operation of a plurality of different exercise sensor devices simultaneously;

establish a plurality of wireless communication links with the counterpart apparatus, wherein each communication link is associated with a different exercise sensor device;

generate exercise-sensor-specific data for each of the plurality of exercise sensor devices; and test compatibility in a multi-sensor environment by outputting the generated measurement data to the display screen for display and to the counterpart apparatus over the communication links in data structures supported by the each of the plurality of exercise sensor devices and selected amongst a plurality of data structures supported by the apparatus for the transfer of the generated measurement data.

15. The apparatus of claim 14, wherein the at least one memory and the computer program code are configured, with the at least one processor, to cause the apparatus to:

receive from the counterpart apparatus scheduling control parameters configuring transmission timing for the plurality of exercise sensor devices; and cause transmission of the generated measurement data of each exercise sensor device in the transmission timing scheduled to said each exercise sensor device.

16. The apparatus of claims 11, wherein the at least one memory and the computer program code are configured, with the at least one processor, to cause the apparatus to:
   receive, through a user interface before the simulation, a selection input from the user selecting at least one exercise sensor device to be simulated; and
   in response to the selection input, select a simulator program corresponding to the selected at least one exercise sensor device.

17. The apparatus of claim 11, wherein the at least one memory and the computer program code are configured, with the at least one processor, to cause the apparatus to:
   when establishing said wireless communication link, determine whether or not the communication link has been established successfully;
   upon detecting failed establishment of the communication link, determine whether or not the failure was because of incompatibility between the exercise sensor device and the counterpart apparatus; and
   upon determining that the failure was because of incompatibility, indicate the incompatibility to the user via the display screen.

18. The apparatus of claim 11, wherein the generated measurement data comprises artificially generated measurement data.

19. The apparatus of claim 11, further comprising at least one sensor, wherein the generated measurement data comprises real measurement data acquired through said at least one sensor of the apparatus.

20. The apparatus of claim 11, wherein the at least one memory and the computer program code are configured, with the at least one processor, to cause the apparatus to download, from a network server computer, program instructions defining simulation parameters for at least one exercise sensor device.

21. A computer program product embodied on a non-transitory distribution medium readable by a computer and comprising program instructions which, when loaded into an apparatus, execute a computer process comprising:
   executing a simulator program capable of simulating operation of a plurality of exercise sensor devices;
   selecting a subset of the plurality of exercise sensor devices for simulation, said subset comprising simulated at least one exercise sensor device;
   establishing a wireless communication link with a counterpart apparatus of a user according to a communication protocol supported by the simulated at least one exercise sensor device;
   generating measurement data representing measurement data generated by said simulated at least one exercise sensor device; and
   testing compatibility between the simulated at least one exercise sensor device and the counterpart apparatus by outputting a parameter dependent on the generated measurement data to the display screen for display and to the counterpart apparatus over the communication link in a data structure used by the simulated at least one exercise sensor device.

* * * * *

UNITED STATES PATENT AND TRADEMARK OFFICE
CERTIFICATE OF CORRECTION

| | | |
|---|---|---|
| PATENT NO. | : 9,454,913 B2 | Page 1 of 1 |
| APPLICATION NO. | : 13/919722 | |
| DATED | : September 27, 2016 | |
| INVENTOR(S) | : Karvonen et al. | |

It is certified that error appears in the above-identified patent and that said Letters Patent is hereby corrected as shown below:

In the Specification

Column 6, Line 29:
Now reads: "parameters to the to the display"
Should read: -- parameters to the display --

Column 9, Line 9:
Now reads: "may further as inputs any"
Should read: -- may further input any --

Signed and Sealed this
Eleventh Day of July, 2017

Joseph Matal
*Performing the Functions and Duties of the*
*Under Secretary of Commerce for Intellectual Property and*
*Director of the United States Patent and Trademark Office*